(12) United States Patent
Kehayias

(10) Patent No.: US 6,314,152 B2
(45) Date of Patent: *Nov. 6, 2001

(54) BODY COMPOSITION DETECTION USING NEUTRON INELASTIC SCATTERING TO DETECT CARBON-TO-OXYGEN RATIO IN TISSUE

(75) Inventor: Joseph J. Kehayias, Chesnut Hill, MA (US)

(73) Assignee: Trustees of Tufts College, Medford, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/931,568

(22) Filed: Sep. 16, 1997

(51) Int. Cl.[7] .................................................. G01N 23/00
(52) U.S. Cl. ................ 376/159; 250/390.04; 250/390.06
(58) Field of Search ....................... 376/159; 250/390.04, 250/390.06

(56) References Cited

PUBLICATIONS

Nucl. Instrum. and Methods in Physics Research A, vol. 353, pp. 444–447, Kehayias et al (I), 1994.*
Proc. SPIE—Int. Soc. Opt. Eng., vol. 2339, pp. 524–528, Kehayias et al (II), 1994.*
Biol. Trace Elem. Res., vol. 26–07, pp. 423–428, Mitra et al, 1990.*
Basic Life Sciences, vol. 60, pp. 49–52, Kehayis et al III, 1993.*
Medical Physics, vol. 20, No. 4, pp. 1129–1134, Sutcliffe et al, Jul./Aug. 1993.*
The American J. of Clinical Nutrition, vol. 61, No. 5, pp. 1110–, Aloia et al (I), May 1995.*
BNL–49461, pp. 1–6, Ma et al, 1993.*
Phys. Med. Biol., vol. 29, No. 3, pp. 209–218, Vartsky et al, 1984.*
Int. S. Nucl. Med. Biol., vol. 4, No. 2, pp. 133–137, Biggin et al, 1977.*
European J. of Clinical Nutrition, vol. 47, pp. 863–874, Ryde et al (I), 1993.*
Metabolism, vol. 34, No. 6, pp. 509–518, Streat et al, 1985.*
Basic Life Sciences, vol. 60, pp. 367–370, Ryde et al (II), 1993.*
J. of Nucl. Med., vol. 36, No. 8, pp. 1392–1397, Aloia et al (II), Aug. 1995.*
Am. J. Physiol: Endocrinology and Metabolism, vol. 24, No. 2, pp. E190–E198, Heymsfield et al, Aug. 1991.*
Phys. Med. Biol., vol. 27, No. 6, pp. 805–817, Kyere et al, 1982.*
J. Radioanal. Nucl. Chem., vol. 160, No. 1, pp. 159–168, Ellis et al, 1992.*

(List continued on next page.)

Primary Examiner—Harvey E. Behrend
(74) Attorney, Agent, or Firm—Hamilton, Brook, Smith & Reynolds, P.C.

(57) ABSTRACT

A technique for determining percent body fat using neutron inelastic scattering is disclosed. It relies on a correlation between a carbon-oxygen ratio in the body and the percent body fat with corrections made for a level of patient hydration in the lean tissue. The animal body is irradiated with neutrons having sufficient energy to inelastically scatter off carbon and oxygen. The resulting gamma rays are detected and counted, and the level of hydration is measured. The ratio of the detected gamma rays and hydration are then related to a proportion of fat in the animal body. This technique provides accuracy approaching that achieved with hydrodensitometry with only small radiation doses between 5 and 20 millirem, but without any requirements for immersion.

15 Claims, 5 Drawing Sheets

OTHER PUBLICATIONS

J.J. Kehayias et al (IV) and H. Zhuang, "Use of the Zetatron D–T Neutron Generator for the Simultaneous Measurement of Carbon, Oxygen, and Hydrogen in vivo in Humans," Nuclear Instruments and Methods in Physics Research Elsevier Science Publishers B.V., NIMB B79 (1993) 555–559.

Joseph J.Kehayias et al (V), "In Vivo Determination of Body Fat by Measuring Total Body Carbon[1-3]," *Am J Clin Nutr* 1991; 53:1339–44.

Richard B. Mazess et al., "Dual–Energy X–ray Absorptiometry for Total–Body and Regional Bone–Mineral and Soft–Tissue Composition[1-2]," *Am J Clin Nutr* 1990; 51:1106–12.

Kenneth R. Foster and Henry C. Lukaski, "Whole–Body Impedance—What Does it Measure[1-2]," *Am J Clin Nutr* 1996; 64(suppl.):388S–96S.

* cited by examiner

BODY COMPOSITION DETECTION USING NEUTRON INELASTIC SCATTERING TO DETECT CARBON-TO-OXYGEN RATIO IN TISSUE

GOVERNMENT SUPPORT

The invention was supported, in whole or in part, by a grant 53-1950-5-003 from United States Department of Agriculture. The Government has certain rights in the invention.

BACKGROUND OF THE INVENTION

Body composition and specifically percent body fat detection is relevant in a number of different contexts. For the individual, it can be used as a predictor of cardiovascular disease. In studies, it is useful to characterize and determine the mechanisms of sarcopenia, defined as the muscle loss with age, and other catabolic conditions. For example, in populations undergoing drug therapy to stall or reverse the effects of wasting diseases such as AIDS, body composition assessment can be used to quantify the efficacy of those drugs.

A number of techniques exist for detecting percent body fat in animals. Hydrodensitometry, bioelectrical impedance analysis (BIA), and dual energy absorptiometry (DXA) are examples based upon the influence of body fat or hydration on physical properties of the body, such as density, electrical impedance, and photon attenuation properties. Other techniques for single compartment body composition analysis are available, some of which are correlated to percent body fat. Body water can be measured by isotope dilution using $D_2O$, $^3H_2O$ or $H_2^{18}O$. Body protein is measured by direct measurement of total body nitrogen (TBN) using prompt-gamma neutron activation. Body cell mass, a compartment overlapping with both water and protein, is measured by gamma counting of the natural radioactivity of the body's $^{40}K$.

SUMMARY OF THE INVENTION

In general these existing techniques for determining percent body fat, although being widely available and in most cases inexpensive, can sometimes fail to yield the accuracy required. In many cases, their assessment of body composition is indirect and subject to a series of assumptions that may vary in their validity across populations of diseased patients. In contrast, the most reliable method is Hydrodensitometry which provides a direct application of the two compartment model using assumptions on the densities of lean and fat tissue. This technique, however, is many times inappropriate, especially in very diseased and older patients since it requires immersion of the patient. Moreover, it typically requires lung volume tests.

The present invention is directed to a technique for determining percent body fat using neutron inelastic scattering. It relies on a correlation between a carbon-oxygen ratio in the body and the percent body fat with corrections made for a level of patient hydration in the lean tissue. This technique provides accuracy approaching that achieved with Hydrodensitometry with only small radiation doses between 5 and 20 millirem, but without any requirements for immersion. It can also measure regional body fat and fat distribution, which is generally not possible using Hydrodensitometry.

In general according to one aspect, the invention features a method for determining proportion of body fat in an animal body. The method includes determining a proportion of body fat as a function of a ratio of carbon and oxygen and levels of hydration. The animal body is then irradiated with neutrons having sufficient energy to inelastically scatter off of carbon and oxygen. The resulting gamma rays are detected and counted. The ratio of the detected gamma rays and hydration are then related to a proportion of fat in the animal body.

In specific embodiments, the level of hydration is preferably directly measured using isotope dilution, for example. Alternatively, the hydration may be estimated based upon the diseased state of the animal body and population statistics relating hydration to the diseased state. Finally, previous hydration tests on a specific individual may be used. However, the technique is not particularly sensitive to the level of hydration.

In other aspects of the embodiment, the proportion of body fat as the function of the ratio of carbon and oxygen includes estimating a portion of detected oxygen that results from water, protein, and fat, and possibly including bone and glycogen, and the corresponding stoichiometries. Similarly, a portion of detected carbon that results from protein and fat is estimated, with the possible inclusion of bone and glycogen.

Where relevant, gamma rays from different regions of the animal body may be detected and separately accounted. This enables the determination of the proportion of fat in those regions.

According to another aspect, the invention features system for determining proportion of body fat in an animal body. The system includes a neutron source, such as a D-T generator, for generating and directing neutrons at the animal body. A gamma ray detector (preferably BGO) detects gamma rays indicative of excited carbon and oxygen atomic nuclei. The controller receives an indication of the detected gamma rays from the gamma ray detector and an input level of hydration for the animal body and determines a proportion of body fat for the animal body.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
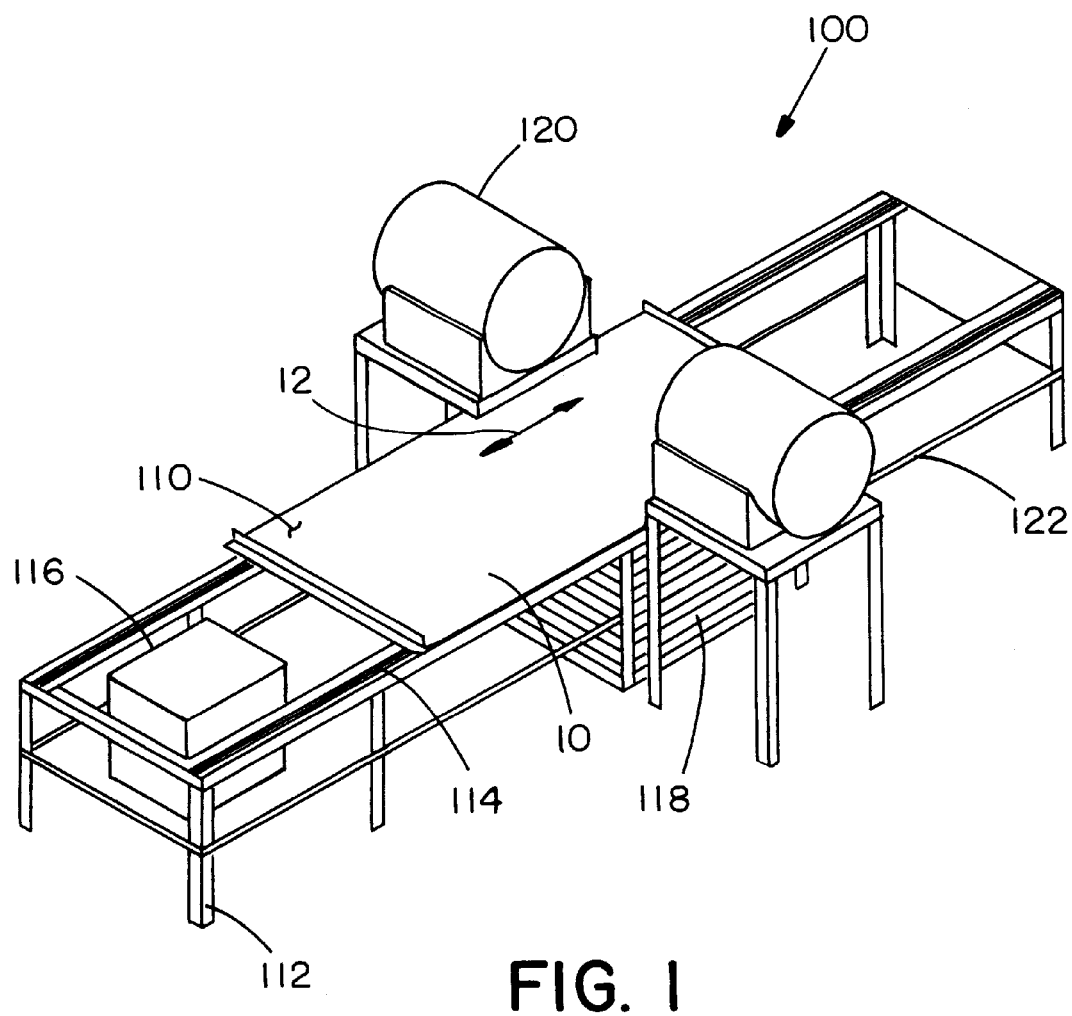
FIG. 1 is a perspective view of neutron inelastic patient scanning device of the inventive system.

FIG. 1 shows a neutron inelastic patient scanning device 100 that is used in accordance with the present invention. A patient 10 lies on the bed 110. A track 114, on which the bed 110 rides, is supported by a frame 112. The bed 110 is propelled on the track by a bed motion control unit 116 to move back and forth in the directions of arrow 12.

Near a mid-portion of the track 114, a shielded high repetition-rate neutron generator 118 is located under the plane of the bed's motion. Two shielded detectors 120, 122 are placed vertically above the generator 118 on either side of the bed 110 and track 114 to detect the gamma rays from neutron inelastic scattering in the patient.

The generator 118 is preferably a sealed, 126 millimeter long tube, which contains an ion source, an accelerator, and a metal tritiated target. A mixture of deuterium and tritium is accelerated at 25–60 keV into the target, resulting in the deuterium-tritium fusion reaction. This produces 14 MeV neutrons. One such D-T generator is sold by Sandia National Laboratories.

The detectors 120, 122 are preferably BGO ($Bi_4Ge_3O_{12}$) crystal detectors. Alternatively, NaI(Tl) detectors may be used. When NaI detectors, however, are exposed to thermal neutrons resulting from multi-scattering of the fast neutron beam, the crystals become activated, which affects the data acquisition performance.

Figure 2:
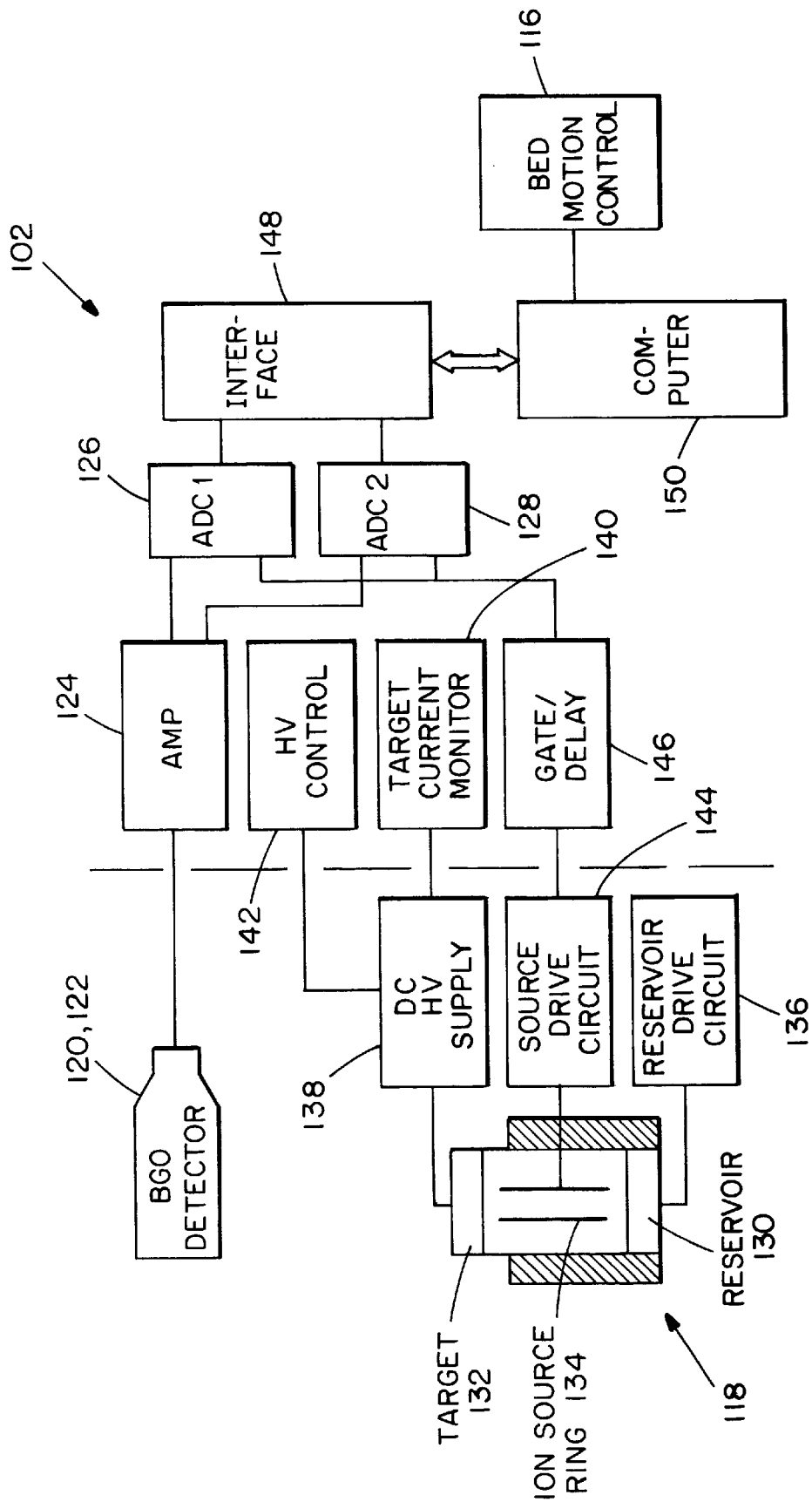
FIG. 2 is a block diagram data acquisition and processing portion of the inventive system.

FIG. 2 is a block diagram illustrating the data acquisition and processing portion 102 of the system. The response of each one of the BGO detectors 120, 122 is supplied to an amplifier 124 and the amplified signal digitized in two analog-to-digital converters 126, 128, which are gated by the neutron pulse.

The D-T neutron generator 118 comprises a reservoir 130 of deuterium and tritium, which is accelerated toward the tritiated target 132 by an ion source ring 134. The reservoir 130 is heated by a reservoir drive circuit 136 and the target is placed at a high electrical potential by the DC voltage supply 138. A target current monitor 140 and high voltage controller 142 are used to ensure that the nuclear reaction at the target is producing the desire quantity of neutrons.

A source drive circuit 144 produces a fast electronic timing signal approximately 1.5 microseconds before the leading edge of the generated neutron pulse. This signal passes through a gate/delay 146 to synchronize the analog-to-digital converters 126, 128 so that two gamma-ray spectra are collected for each detector. As a result, the analog-to-digital converters 126, 128 are triggered to detect the gamma-rays simultaneously within a 10–20 microsecond long neutron pulse.

The digital data from the analog-to-digital converters 126, 128 are passed to a system controlling computer 150 through an interface 148. The computer additionally receives bed positional information from the bed motion control unit 116. This allows the computer to correlate instantaneous gamma ray counts to the regions of the patient's body that are currently being irradiated.

Figure 3:
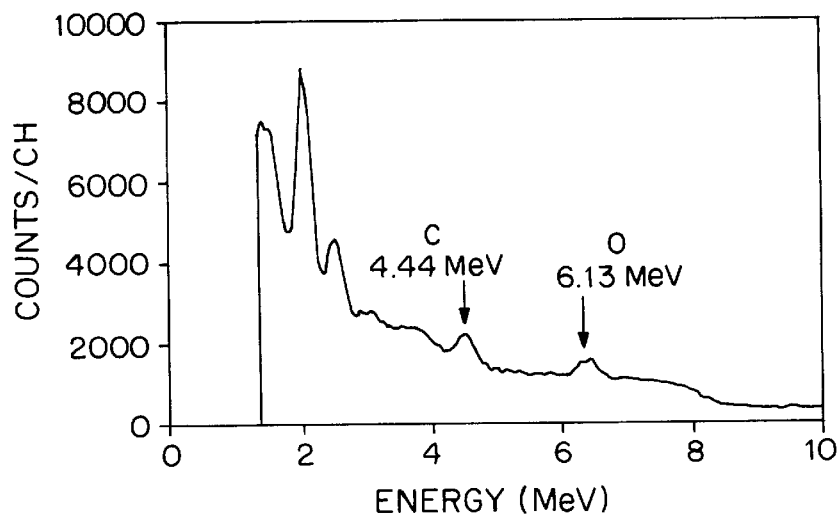
FIG. 3 is plot of detected gamma ray counts as a function of energy showing carbon and oxygen peaks in the spectra.

FIG. 3 is an exemplary spectra detected from a patient. The identified peaks at 4.44 MeV and 6.13 MeV arise from the inelastic scattering of the neutrons off of carbon and oxygen atomic nuclei.

According to the following derivation, the ratio of these two peaks in the spectra, indicating the carbon-to-oxygen ratio, is correlated to the percent body fat in the patient.

The components of lean body mass are water, protein (pro), bone ash (ba) and glycogen (gly).

$$Lean=Water/Coeff \qquad (1)$$

For the purposes of body composition analysis, glycogen can be derived from protein:

$$gly=0.044*pro \qquad (2)$$

Neutron activation analysis for the in vivo measurement of total body calcium (TBCa) and nitrogen (TBN) has shown that there is a strong correlation between ba and pro.

$$TBCa=0.612*TBN(R=0.999, p<0.00001),$$

which results to a correlation between bone ash and protein.

$$ba=TBCa/0.383$$

$$pro=6.26*TBN, then$$

$$ba=0.255*pro \qquad (3)$$

Combining the above equations with the observation that $$pro=Lean-Water-ba-gly \qquad (4)$$

the body compartments are expressible in terms of body weight (Wt), Water and Coeff:

$$Lean=Water/Coeff$$

$$pro=0.770*A$$

$$gly=0.034*A$$

$$ba=0.196*A$$

$$Fat=Wt-Water/Coeff \qquad (5)$$

where $A=Water*[1/Coeff-1]$ and represents the portion of lean which is not water.

Although each of the above assumptions is based on a well developed correlation between portions of lean, when taken together they state a constant partition of lean to its components.

The contributing compartments of total body carbon (TBC) are fat, protein, glycogen and bone ash. The stoichiometry of each compartment is accounted for to calculate TBC.

Fat is accurately represented by the stoichiometry $C_{55}H_{102}O_6$. In spite of some variation in the composition of triglycerides, the average stoichiometry of fat is constant, at least in its carbon content of 77%. According to a classic meat amino acid profile ($C_{100}H_{159}N_{26}O_{32}S_{0.7}$), protein contains 53.1% carbon by weight. Glycogen ($C_6H_{10}O_5$) contains 44.4% carbon. Bone ash contains 1.73% carbon.

$$TBC=0.769*Fat+0.531*pro+0.444*gly+0.0173*ba \qquad (6)$$

using equations (2) and (3), $$TBC=0.769*Fat+0.555*pro \qquad (7)$$

Similarly, the contributing compartments to total body oxygen (TBO) are water, protein, fat, bone ash and glycogen. Taking into account the oxygen content of these compartments:

$$TBO = 0.888*Water + 0.226*pro + 0.112*Fat + 0.416*ba*0.493*gly \quad (8)$$

or $$TBO = 0.888*water + 0.354*pro + 0.112*fat \quad (9)$$

Combining equations (7) and (9) and using (5), expression for the ratio of total carbon to total oxygen is derived.

$$C/O = \frac{0.769*(Wt - Water/Coeff) + 0.427*Water*(1/Coeff - 1)}{0.888*Water + 0.273*Water(1/Coeff - 1) + 0.112*(Wt - Water/Coeff)} \quad (10)$$

$$C/O = \frac{0.769 - \frac{Water}{Wt} * \left(\frac{0.342}{Coeff} + 0.427\right)}{0.112 + \frac{Water}{Wt} * \left(\frac{0.161}{Coeff} + 0.615\right)}$$

Equation (10) describes carbon-oxygen ratio (C/O) as a function of the hydration coefficient of lean, Coeff, and the total amount of water in the body expressed as a fraction of body weight. From the expression for Fat in equation (5), it is observed that $$Fat/Wt = 1 - \frac{Water}{Wt} * \frac{1}{Coeff} \quad (11)$$

so, for each value of fat content (Fat/Wt), there is a corresponding value of Water/Wt:

$$Water/WT = Coeff * \left(1 - \frac{Fat}{Wt}\right) \quad (12)$$

Using (12) equation (10) becomes:

$$C/O = \frac{0.769 - (1-F)*(0.342 + 0.427*Coeff)}{0.112 + (1-F)*(0.161 + 0.615*Coeff)} \quad \text{or} \quad (13)$$

$$F = \frac{0.273*C/O + 0.427*Coeff + 0.615*Coeff*C/O - 0.427}{0.161*C/O + 0.427*Coeff + 0.615*Coeff*C/O + 0.342} \quad (14)$$

If a hydration coefficient of lean body mass is assumed or detected to be 0.732, for example, the relationship between fat content and the C/O ratio becomes:

$$F = \frac{0.723*C/O - 0.114}{0.611*C/O + 0.655} \quad (15)$$

where F is the fat content: Fat/Wt. This equation describes a non-linear relationship between fat content and C/O ratio for a given hydration coefficient of lean.

Figure 4:
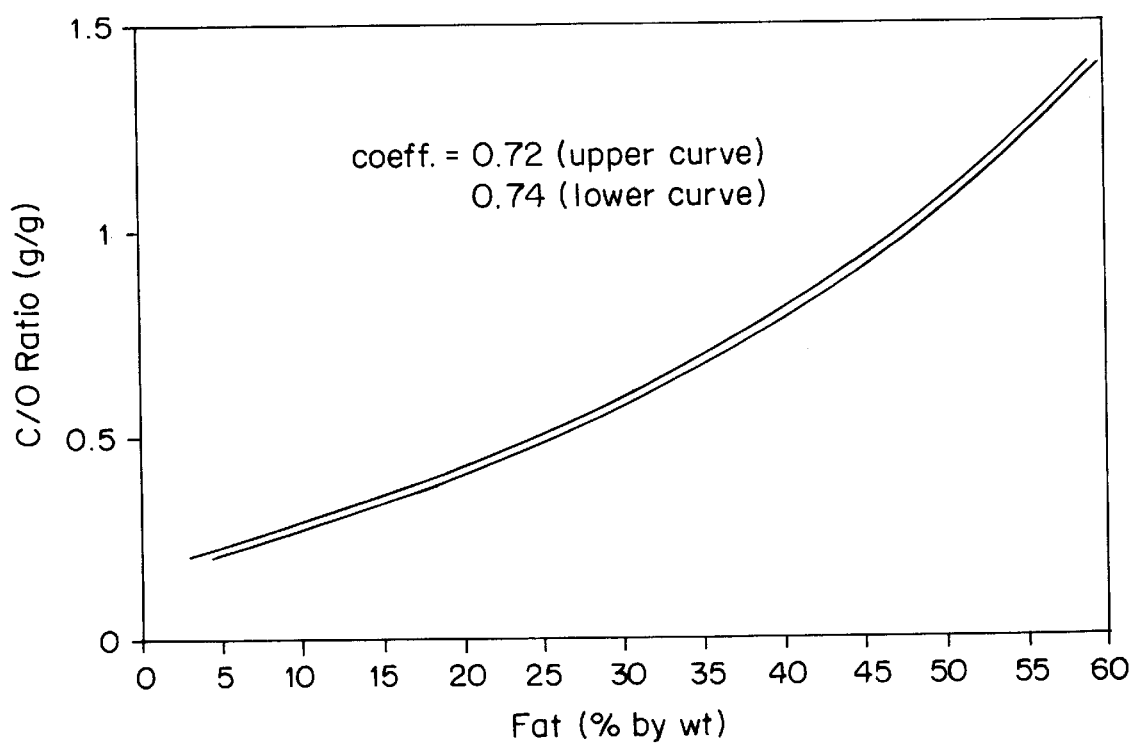
FIG. 4 is a plot of the measured carbon-oxygen ratio as a function of percent body fat for two assumed levels of hydration.

Incidently, the equation (14) relating percent body fat to the carbon-oxygen ratio and hydration coefficient of lean body mass is relatively insensitive to error in the hydration coefficient. FIG. 4 is a plot of the carbon-oxygen ratio as a function of calculated percent body fat for hydration coefficients of 0.720 and 0.740. An error in the hydration coefficient results in a only a few percent deviation in the measure percent body fat.

Figure 5:
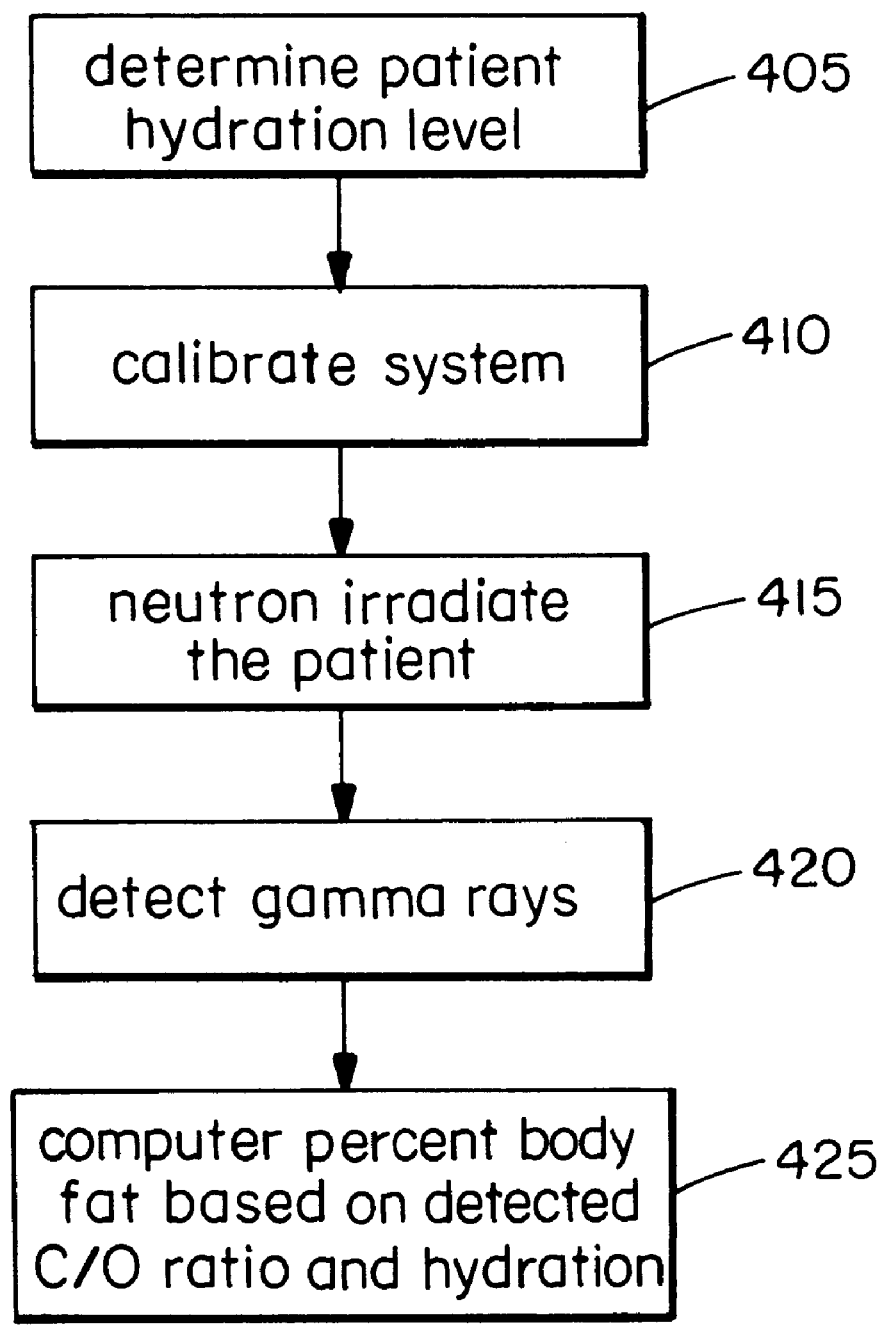
FIG. 5 is a diagram illustrating the method for determining proportion of body fat in an animal body.

FIG. 5 is a method diagram illustrating the technique for determining percent body fat according to the principles of the present invention.

The above derived formula relates the percent body fat to a carbon/oxygen ratio and a level of hydration. While the formula includes contributions from bone ash and glycogen, these two components represent a relatively small part of the total carbon and oxygen in individuals. As a result they can be excluded from the analysis or estimated indirectly without degrading the accuracy in some applications.

In step 405, the level of hydration is determined according to any one of a number of separate approaches. First, the level of hydration can be simply assumed. For most healthy populations, the hydration coefficient for lean body mass is 0.732. Such an assumption, however, in many circumstances will not provide the required level of accuracy. As a result, a separate direct hydration measurement can be performed. A number of different techniques may be used. Isotope dilution using deuterium, tritium, or $H_2^{18}O$ is one possibility.

The level of hydration of the lean tissue, however, is also determined by using data in some cases. One of two techniques may be used. First, if the patient is diseased, data concerning the hydration for the diseased population provides a good predictor. For example, levels of hydration tend to be higher in patients with diabetes. Population data for other individuals having similar hydration effecting syndromes establish the lean tissue hydration for the patient being tested. Secondly, if the hydration of this patient has been previously measured, that direct measurement can be used in place of a contemporaneous measurement.

Prior to irradiation, the system described with reference to FIGS. 1 and 2 is calibrated in step 410. This should be performed on at least daily basis since changes in atmospheric pressure and aging of the generator 118 can affect operation and thus accuracy. In the preferred embodiment, a substance with a known carbon-oxygen ratio is placed in the detector and the detected carbon-oxygen ratio used to calibrate it. For example, sugar is one possibility.

In step 415, the patient is irradiated with neutrons. For this technique involving neutron inelastic scattering, the neutrons must have sufficient energy to excite the nuclei of carbon and oxygen atoms to their a first energy level. For carbon, this requires neutrons having energy of greater than 4.8 MeV, and for oxygen, neutrons having an energy greater than 6.3 MeV are required.

In the preferred embodiment, the animal body is irradiated with the neutrons in bursts. During those bursts, the number of generated gamma rays is detected using the BGO detectors 120, 122 in step 420. The system processor or computer 150 receives the gamma ray count and energy information from analog to digital converters 126, 128. This raw data is then corrected using the information from the calibration step.

Also during the irradiation, the patient is scanned between the D-T generator 118 and BGO detectors 120, 122. This allows the determination of a net or average carbon-oxygen ratio for the entire body of the patient. The system controller 150, however, also saves the detected gamma rays for regions of the body using the feedback from the bed motion control 116. As a result, the carbon-oxygen ratio for these regions may be also simultaneously determined. For example, the system controller saves the number of gamma rays detected while scanning the lower leg, thigh, lower abdominal region, mid abdominal region, and chest region separately.

In the preferred embodiment, the patient is repeatedly scanned over the neutron source is a oscillatory fashion for approximately 30 minutes. The time period allows sufficient data to be collected while maintaining a low total radiation dose without becoming too onerous for the patient.

One advantage associated with the present invention is that it operates based upon the carbon-oxygen ratio. Previous attempts based upon total body carbon or total body nitrogen have been more sensitive to the particular operation of the neutron generator and detector since they rely on total counts. As a result, if the detector is operating less efficiently, or if the neutron generator is generating fewer neutrons with the appropriate energies, the accuracy of the measurement will be affected and also require more frequent calibration. In the present invention, a ratio is used that factors out effects of slight aging of the detector and generator.

In the final step, the system controller 150 after having received the hydration data, then uses the measured carbon-oxygen ratio to produce a measure of the percent body fat in step 425. This measure is corrected based upon the information from the calibration and the assumed, or measured level of hydration. Moreover, combining the detected neutron counts with the bed position information yields the fat composition for regions of the patient's body.

Figure 6:
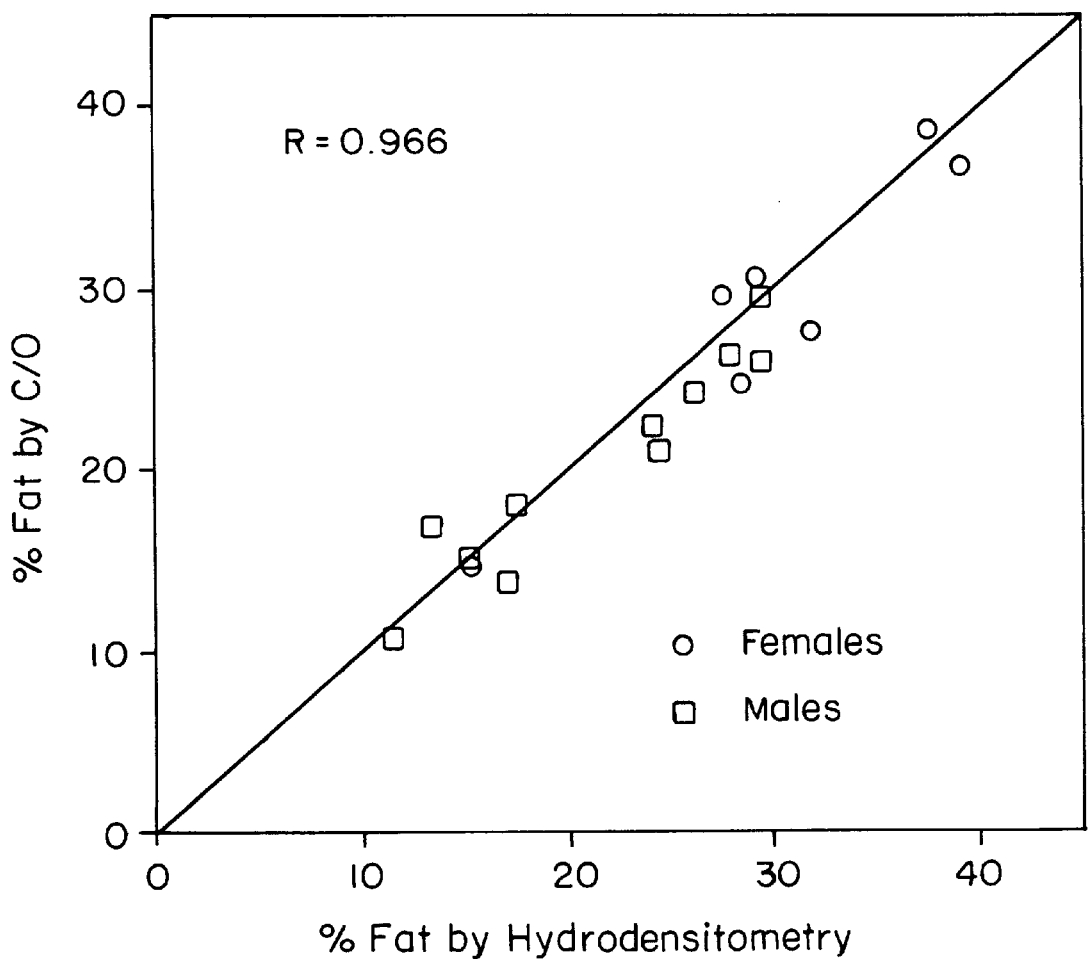
FIG. 6 is a plot of percent body fat as measured by the carbon-oxygen ratio (vertical scale) and hydrodensitometry (horizontal scale).

FIG. 6 is plot of percent body fat as measured by the carbon-oxygen ratio and hydrodensitometry. The demonstrates the accuracy of the inventive technique based on the close agreement the accepted and established hydrodensitometry.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims. For example, the hydration level measurement may be performed at any time, before or after the neutron scan.

What is claimed is:

1. A method for determining proportion of body fat in an animal body the method comprising:

irradiating the animal body with neutrons having sufficient energy to inelastically scatter off carbon and oxygen, and thereby produce gamma rays;

detecting produced gamma rays from the animal body that are indicative of carbon and oxygen that have been excited by said neutrons;

providing a level of hydration of lean tissue (Coeff) of the animal body;

generating a ratio of the detected gamma rays from carbon and oxygen (C/O); and determining the proportion of body fat (F) in the animal body as a function of the ratio of carbon and oxygen (C/O) and the level of hydration of lean tissue (Coeff) according to the formula:

$$F = \frac{a_1 * C/O + a_2 * Coeff + a_3 * Coeff * C/O - a_2}{a_4 * C/O + a_2 * Coeff + a_3 * Coeff * C/O + a_5}$$

where $a_1$, $a_2$, $a_3$, $a_4$, and $a_5$ are constants derived from the stoichiometry of one or more of the following chemical compartments: triglycerides, water, protein, bone ash, and glycogen.

2. A method as described in claim 1, wherein the step of providing the level of hydration of lean tissue comprises performing a direct hydration measurement.

3. A method as described in claim 2, wherein the step of performing the direct hydration measurement comprises performing isotope dilution.

4. A method as described in claim 1, wherein the step of providing the level of hydration of lean tissue comprises estimating the level of hydration based upon a diseased state of the animal body.

5. A method as described in claim 1, wherein the step of providing the level of hydration of lean tissue comprises estimating the level of hydration based upon hydration levels in a healthy population.

6. A method as described in claim 1, wherein the step of determining the proportion of body fat comprises estimating a portion of detected oxygen that results from water, protein, and fat.

7. A method as described in claim 6, further comprising estimating the portion of detected oxygen that results from bone and glycogen.

8. A method as described in claim 6, wherein the step of estimating the portion of detected oxygen that results from water, protein, and fat comprises determining the stoichiometry of water, protein, and fat.

9. A method as described in claim 1, wherein the step of determining the proportion of body fat comprises estimating a portion of detected carbon that results from protein and fat.

10. A method as described in claim 9, further comprising estimating the portion of detected carbon that results from bone and glycogen.

11. A method as described in claim 9, wherein the step of estimating the portion of detected carbon that results from water and fat comprises determining the stoichiometry of water and fat.

12. A method as described in claim 1, performing a calibration by irradiating a substance having a known ratio of carbon and oxygen.

13. A method as described in claim 1, further comprising detecting the gamma rays from different regions of the animal body to determine a proportion of fat in those regions.

14. A method as described in claim 1, wherein the step of detecting the gamma rays from the different regions comprises scanning a gamma ray detector along the animal body and counting the gamma rays detected for each of the individual regions.

15. A method for determining the proportion of body fat in individuals by neutron inelastic scattering, the method comprising:

irradiating the individuals within diseased or normal populations with neutrons having sufficient energy to inelastically scatter off of carbon and oxygen, and thereby produce gamma rays;

detecting produced gamma rays from the individuals that are indicative of carbon and oxygen that have been excited by said neutrons;

providing levels of hydration of lean tissue (Coeff) for the diseased and/or normal populations;

generating a ratio of the detected gramma rays from carbon and oxygen (C/O) to estimate the proportion of fat (F) in the individuals; and using said ratio of carbon to oxygen and the provided levels of hydration of lean tissue (Coeff) for the diseased and/or normal populations to correct the estimated proportion of fat (F) in the individuals according to the formula:

$$F = \frac{a_1 * C/O + a_2 * Coeff + a_3 * Coeff * C/O - a_2}{a_4 * C/O + a_2 * Coeff + a_3 * Coeff * C/O + a_5}$$

where $a_1$, $a_2$, $a_3$, $a_4$, and $a_5$ are constants derived from the stoichiometry of one or more of the following chemical compartments: triglycerides, water, protein, bone ash, and glycogen.

* * * * *